(12) United States Patent
Papas

(10) Patent No.: US 6,273,914 B1
(45) Date of Patent: Aug. 14, 2001

(54) SPINAL IMPLANT

(75) Inventor: Gary R. Papas, San Diego, CA (US)

(73) Assignee: Sparta, Inc., Laguna Hills, CA (US)

( * ) Notice: Subject to any disclaimer, the term of this patent is extended or adjusted under 35 U.S.C. 154(b) by 0 days.

(21) Appl. No.: 08/999,906

(22) Filed: Dec. 2, 1997

(Under 37 CFR 1.47)

Related U.S. Application Data

(63) Continuation of application No. 08/535,568, filed on Sep. 28, 1995, now abandoned.

(51) Int. Cl.[7] ............................... A61F 2/44; A61B 17/70
(52) U.S. Cl. ............................ 623/17.11; 606/61
(58) Field of Search ........................ 606/61; 623/17.11

(56) References Cited

U.S. PATENT DOCUMENTS

| | | | |
|---|---|---|---|
| 4,369,769 | 1/1983 | Edwards | 128/69 |
| 5,129,899 | 7/1992 | Small et al. | 606/61 |
| 5,181,930 | 1/1993 | Dumbleton et al. | 623/23 |
| 5,352,224 | 10/1994 | Westermann | 606/61 |
| 5,425,772 | 6/1995 | Brantigan | 623/17 |
| 5,509,933 | 4/1996 | Davidson et al. | 623/16 |

Primary Examiner—Corrine McDermott
Assistant Examiner—Choon P. Koh
(74) Attorney, Agent, or Firm—Stetina Brunda Garred & Brucker

(57) ABSTRACT

A spinal implant for rigid fixation of at least two vertebrae of a pine has at least one support member configured for attachment to the vertebrae and is comprised of a biocompatible polymer composite. A plurality of fasteners attach the support members to the vertebrae. A predefined standard selection of such bio-compatible implant components Ore provided so as to define support members which conform to the specific anatomical structure of the patient's spine without being modified.

13 Claims, 4 Drawing Sheets

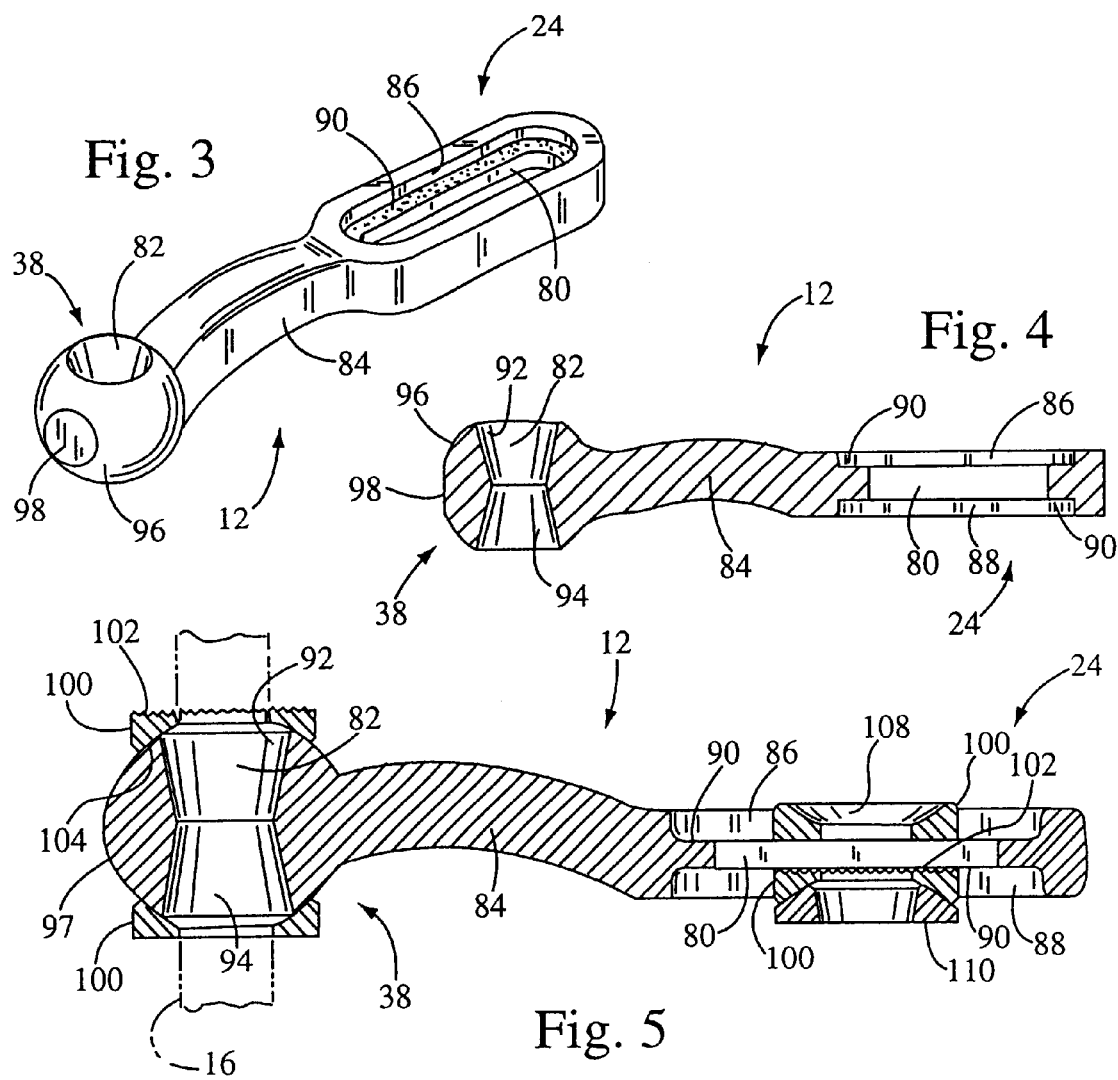
Fig. 3
Fig. 4
Fig. 5
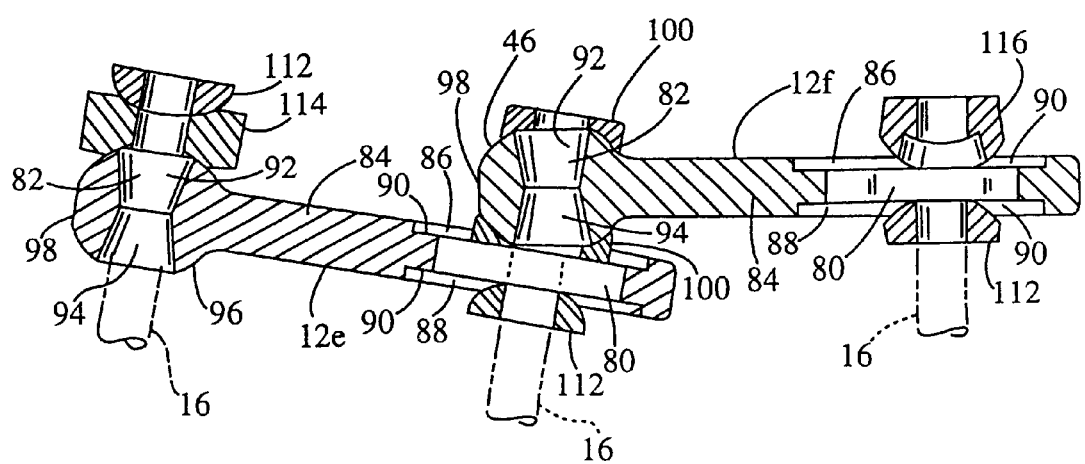
Fig. 6

SPINAL IMPLANT

This application is a continuation, of application Ser. No. 08/535,568, filed Sep. 28, 1995 now abandoned.

FIELD OF THE INVENTION

The present invention relates generally to orthopedic medical devices and more particularly to a spinal implant for tissue stabilization involving at least two spinal vertebrae.

BACKGROUND OF THE INVENTION

Spinal implants for aligning the spine and maintaining desired spacing of the vertebrae for spinal fusion procedures are well known. Such spinal implants typically comprise a pair of stainless steel rods which extend longitudinally along that portion of the spine to be fused and which attach to the vertebrae via clamps. The clamps are typically attached to the rods via set screws which engage each rod at a desired point along the length thereof as the rod passes through an aperture formed within the clamp. Thus, by tightening the set screw, the rod is held in place relative to the clamp. Threaded fasteners, i.e., self tapping screws, extend through the clamps and engage the lateral mass of the sacrum and/or the transverse processes of desired vertebrae. Thus, a plurality of such clamps attach each rod to the spine.

However, in order to accommodate the specific anatomical structure of a particular patient's spine, the rods must commonly be modified, i.e., bent. As those skilled in the art will appreciate, each individual patient's spine is structurally unique, i.e., having unique curvature and having a lateral masses and transverse processes of different sizes, shapes, and locations, thereby necessitating such bending of the rods utilized according to the prior art. Thus, the method for attaching such contemporary spinal implants comprises repeatedly positioning the rods along the spine to determine the amount of bending necessary, and then bending the rods so as to cause them to conform to the configuration required by that particular patient's specific anatomical configuration. Thus, it commonly requires several attempts, i.e., trial placements and bending of the rods, in order to achieve adequately configured, i.e., bent, rods which conform to a particular patient's anatomy.

Not only is such modification or bending of the rods inconvenient and time consuming, but it also increases the risks to the patient associated with the surgical procedure. Increasing the length of time during which the spine must be exposed in order to facilitate such modification of the rods inherently increases the risk of infection. Additionally, a greater amount of anesthetic is required in order to maintain the patient in the required anesthetized condition for such a prolonged period of time. As those skilled in the art are aware, substantially increased risk is associated with increased anesthetic.

Further, each attach point, i.e., the point where each rod is attached to a vertebra via a clamp, comprises two different threaded fasteners, the loosening of either of which results in undesirable loss of support at that attach point. Thus, if either the set screw which attaches the clamp to the rod or the screw which attaches the clamp to a vertebra loosens after completion of the surgical implant procedure, then the vertebra associated therewith does not receive sufficient support for rigid fixation or tissue stabilization, and thus injury to the patient may occur and/or additional surgery may be required.

As those skilled in the art will appreciate, all of the various components associated with such implants, i.e., the rods, clamps, set screws, and screws, must be comprised of a bio-compatible material. To date, only stainless steel and titanium have been found to possess both the required structural strength and adequate bio-compatibility. However, even these materials may degrade upon prolonged exposure to biological environments. Further, metal components are difficult to modify, i.e., bend and inhibit post-operative imaging.

As such, although the prior art has recognized to a limited extend the problem of providing a spinal implant for tissue stabilization of a portion of the spine, the proposed solutions have, to date, only achieved limited success in providing a satisfactory remedy.

Thus, it would be beneficial to provide a spinal implant comprised of a material having greater bio-compatibility than stainless steel or titanium and which is suitable for long-term use and which also does not require modification during the surgical implant procedure and allows enhanced post-operative imaging capability. It would further be beneficial to provide a spinal implant which utilizes standardized components in order to eliminate the requirement for routine modification during the surgical procedure.

SUMMARY OF THE INVENTION

The present invention specifically addresses and alleviates the above-mentioned deficiencies associated with the prior art. More particularly, the present invention comprises a plurality of standardized bio-compatible components which may be assembled in a manner which accommodates the individual variations inherent in a particular patient's anatomy. The standardized components of the present invention attach to one another and to a patient's vertebrae in a manner which facilitates various different orientations or configurations of the components with respect to one another and with respect to the patient's vertebrae. Thus, by utilizing a minimum number of different standardized components, rigid fixation of the spine may be achieved without requiring modification of any of the components.

More particularly, the present invention comprises a spinal implant for rigid fixation of at least two vertebrae of a spine wherein the spinal implant comprises at least one support member configured for attachment to the vertebrae, the support member being formed of a bio-compatible polymer composite, and a plurality of fasteners for attaching the support member to the vertebrae. In the preferred embodiment of the present invention, the fasteners are comprised of stainless steel. However, those skilled in the art will appreciate that various different bio-compatible materials are likewise suitable.

According to the preferred embodiment of the present invention, the bio-compatible polymer composite comprises carbon/PEEK composite, preferably comprising approximately 60% carbon fiber. The carbon fiber preferably comprises bulk molded carbon fiber, preferably having a length of approximately ⅜ inch.

More particularly, the support members of the present invention preferably comprises a plurality of links for extending along the spine so as to define first and second generally parallel longitudinally extending supports. The links cooperate to rigidly fix at least two adjacent vertebrae relative to one another.

Optionally, the support members of the present invention further comprise a plurality of cross-members extending between the first and second longitudinally extending supports such that the links and cross-members cooperate to rigidly fix at least two adjacent vertebrae relative to one another.

For example, a first link is attachable at the first end thereof to the left lateral mass of the sacrum and is similarly attachable at the second end thereof to the left transverse process of the fifth lumbar vertebra. Similarly, a second link is attachable at the first end thereof to the left transverse process of the fifth lumbar vertebra and is attachable at the second end thereof to the left transverse process of the fourth lumbar vertebra. The first and second links thus cooperate to define a first support.

In a like manner, a third link is attachable at the first end thereof to the right lateral mass of the sacrum and is attachable at the second end thereof to the right transverse process of the fifth lumbar vertebra. Similarly, a fourth link is attachable at the first end thereof to the right transverse process of the fifth lumbar vertebra and is attachable at the second end thereof to the right transverse process of the fourth lumbar vertebra. The second and third links thus cooperate to define a second support.

A first cross-member is attachable at the first end thereof to the left lateral mass of the sacrum and is attachable at the second end thereof to the right transverse process of the fourth lumbar vertebra. Similarly, a second cross-member is attachable at a first end thereof to the right lateral mass of the sacrum and is attachable at the second end thereof to the left transverse process of the fourth lumbar vertebra. The first and second cross-members thus cooperate to enhance the rigidity of the first and second supports.

Thus, the first, second, third, and fourth links and the first and second cross-members cooperate to rigidly fix the fourth lumbar vertebra, the fifth lumbar vertebra, and the sacrum relative to one another.

The first, second, third, and fourth links and the first and second cross-members comprise a slot formed in at least one of the first and second ends thereof, so as to facilitate variability in distance between where the first and second ends thereof attach to the spine. Preferably the first, second, third, and fourth links and the first and second cross-members comprise a slot formed at one of the first and second ends thereof and an aperture formed at the other of the first and second ends thereof. The slot facilitates longitudinal movement of support members relative to one another prior to tightening the fastener that passes therethrough, thus allowing the spinal implant of the present invention to self-adjust or configure itself to the anatomy of the patient. The slots also allow for flexibility in selecting the attach points on the spine by allowing variance in the distance therebetween.

The support members, i.e., the links and cross-members, preferably facilitate angular movement of support members relative to one another within one plane so as to provide a single degree of freedom, as in a hinge type of arrangement. The spinal implant optionally comprises at least one adapter for attaching to the planar attachment surface of a support member and for providing a non-planar surface so as to facilitate angular movement of support members relative to one another within more than one plane, as in a ball and socket type of arrangement. The adapter is preferably configured for attachment to a planar surface of a slot so as to facilitate both longitudinal and angular movement of support members relative to one another. The slot facilitates longitudinal movement of the support members relative to one another and the non-planar surface of the adapter facilitates angular movement of the support members relative to one another.

Thus, the support members preferably comprise a non-planar surface so as to facilitate angular movement of support members relative to one another within more than one plane. The non-planar surface preferably comprises a generally spherical surface, so as to provide three degrees of freedom, i.e., two angular and one rotational, between interconnected support members. Thus, when such a non-planar surface is utilized along with a slot, a total of 4 degrees of freedom are provided. The non-planar surface provides two angular and one rotational degree of freedom and the slot provides one translational degree of freedom.

The fasteners preferably comprise threaded fasteners, preferably threaded studs having a tapered thread formed upon one end thereof configured for self-threading into and engaging a vertebra and also having a non-tapered thread formed upon the opposite end thereof for engaging a nut, such that at least one support member is capturable intermediate the nut and the vertebra. Thus, tightening the fastener, typically via tightening the nut threaded thereon, results in clamping of the support member intermediate the nut in the vertebra, so as to rigidly attach the support member to the vertebra.

Thus, according to the present invention at least one, preferably two support members, i.e., two links or one link and one cross-member, are attached to the spine at each attach point via a threaded fastener wherein rigidity of the support members relative to one another and relative to the vertebrae to which they are attached is achieved by tightening the nut of the fastener so as to clamp the ends of the support members to a vertebra at the attach point.

In those instances wherein only a single degree of freedom is required, support members are attached to one another via a planar interface. In those instances wherein more than one degree of freedom is required, support members are attached to one another via a non-planar, preferably generally spherical, e.g., ball-and-socket, type of interface. Those skilled in the art will appreciate that various other types of interfaces are likewise suitable.

These, as well as other advantages of the present invention will be more apparent from the following description and drawings. It is understood that changes in the specific structure shown and described may be made within the scope of the claims without departing from the spirit and scope of the invention.

BRIEF DESCRIPTION OF THE DRAWINGS

FIG. 3 is a perspective view of a single link of the spinal implant of the present invention;

FIG. 4 is a cross-sectional side view of the link of FIG. 3;

FIG. 5 is an enlarged cross-sectional side view of the link of FIGS. 3 and 4, also showing two adapters attached to the generally spherical end thereof for providing a planar interface to a link or cross-member and also showing two adapters disposed within the slot thereof for attaching the link to the spherical end of another link;

FIG. 6 is a cross-sectional view showing the attachment of two links to one another utilizing a ball-and-socket configuration;

DETAILED DESCRIPTION OF THE PREFERRED EMBODIMENT

The detailed description set forth below in connection with the appended drawings is intended as a description of the presently preferred embodiment of the invention, and is not intended to represent the only form in which the present invention may be constructed or utilized. The description sets forth the functions and sequence of steps for constructing and operating the invention in connection with the illustrated embodiment. It is to be understood, however, that the same or equivalent functions and sequences may be accomplished by different embodiments that are also intended to be encompassed within the spirit and scope of the invention.

Figure 1:
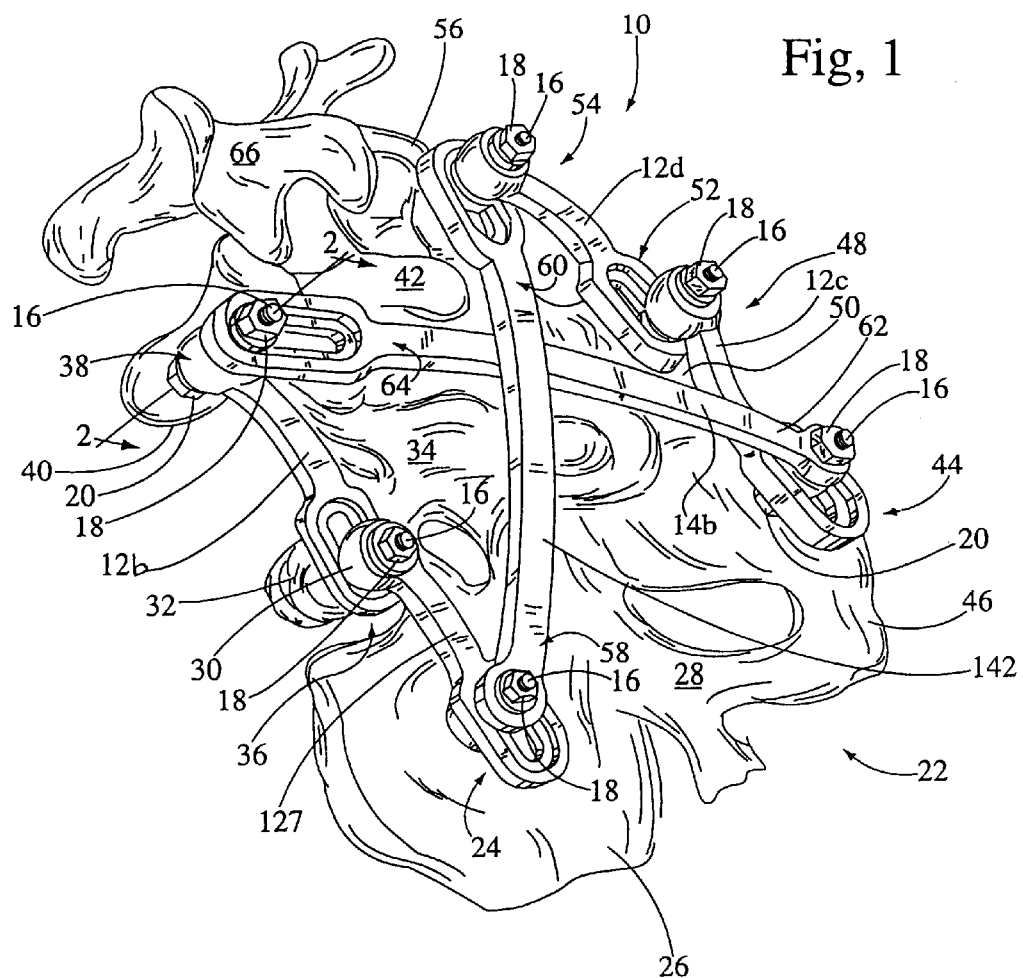
FIG. 1 is an overall perspective view of the spinal implant of the present invention attached to a spine so as to provide rigid fixation of the fourth and fifth lumbar vertebrae relative to the sacrum.

The spinal implant of the present invention is illustrated within FIGS. 1–13 of the drawings which depict a presently preferred embodiment of the invention. Referring now to FIG. 1, the spinal implant 10 of the present invention is comprised generally of a plurality of support members, i.e., links and cross-members, configured for attachment to desired vertebrae of the spine. More particularly, the support members comprise four links 12a–d and two cross-members 14a and 14b.

A plurality of fasteners, preferably threaded studs 16, preferably have spaced apart upper 18 nuts and lower 20 nuts for attaching the links 12a–d and cross-members 14a, 14b to one another and to the spine 22. The lower 20 nuts may optionally be omitted, as desired.

According to the exemplary implant illustrated in FIG. 1, the first link 12a is attached at the lowermost or first end 24 thereof to the left lateral mass 26 of the sacrum 28 and is attached at the upper or second end 30 to the left transverse process 32 of the fifth lumbar vertebra 34.

The second link 12b is attached at the lower or first end 36 thereof to the left transverse process 32 of the fifth lumbar vertebra 34 and is attached at the upper or second end 38 thereof to left transverse process 40 of fourth lumbar vertebra 42.

The third link 12c is attached at the lower or first end 44 thereof to right lateral mass 46 of the sacrum 28 and is attached at the upper or second end 48 thereof to the right transverse process 50 of the fifth lumbar vertebra 34.

The fourth link 12d is attached at the lower or first end 52 thereof to the right transverse process 50 of the fifth lumbar vertebra and is attached at the upper or second end 54 thereof to the right transverse process 56 of the fourth lumbar vertebra 42.

The first cross-member 14a is attached at the lower or first end 58 thereof to the left lateral mass of the sacrum 28 and is attached at the upper or second end 60 thereof to the right transverse process 56 of the fourth lumbar vertebra 42.

The second cross-member 14b is attached at the lower or first end 62 thereof to the right lateral mass 46 of the sacrum 28 and is attached at the upper or second end 64 to the left transverse process 40 of the fourth lumbar vertebra 42.

Thus, the first 12a, second 12b, third 12c, and fourth 12d links and the first 14a and second 14b cross-members cooperate to rigidly fix the fourth lumbar vertebra 42, the fifth lumbar vertebra 34, and the sacrum 28 relative to one another. The third lumbar vertebra 66 is not rigidly fixed relative to the fourth lumbar vertebra 42, the fifth lumbar vertebra 34, and/or the sacrum 28, and is thus free to move relative thereto.

Each link 12a–12b and each cross-member 14a–14b is preferably bowed slightly so as to allow it to be disposed over boney protuberances and/or other anatomical structures or components of the spinal implant of the present invention. The links 12a–12b and the cross-members 14a–14b may be disposed such that they are either bowed in an upward direction or in a downward direction, as desired, during the surgical implant procedure. Thus, further flexibility in the configuration of the spinal implant is provided.

Figure 2:
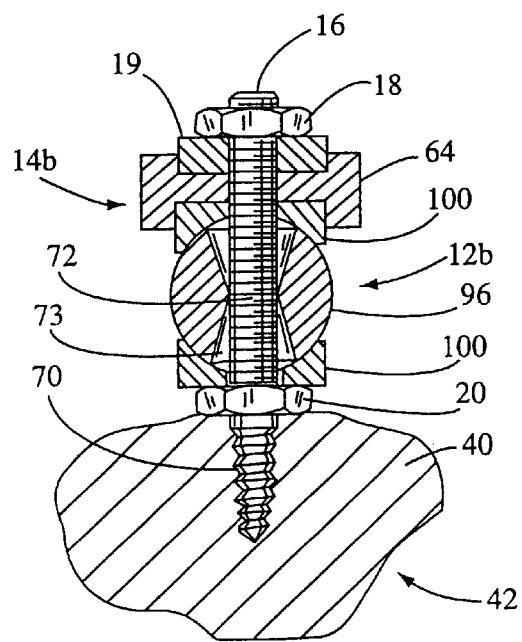
FIG. 2 is a cross-sectional side view of a typical attach point, taken along lines 2 of FIG. 1, showing a non-planar, i.e., generally spherically, interface for providing four degrees of freedom, i.e., two angular, one rotational, and one lateral, between attached support members.

Referring now to FIG. 2, a typical attachment point is illustrated. The other attach points are generally analogous in structure and function to that illustrated. At this particular attachment point, a fastener comprising threaded stud 16 and upper 18 and lower 20 nuts attaches the second link 12b and the second cross-member 14b to the left transverse process 40 of the fourth lumbar vertebra 42. Tapered threads 70 anchor the threaded stud 16 into the left transverse process 40 of the fourth lumbar vertebra 42. The use of such tapered threads 70 facilitates easy attachment of the links 12a–b and cross-members 14a, b to the spine 22, as discussed in detail below. Non-tapered threads of threaded stub 72 engage the upper 18 and lower 20 nuts such that they may be tightened so as to clampably engage and capture the second link 12b and the second cross-member 14b. The lower nut 20 optionally also functions as a jam nut against the left transverse process 40 of the fourth lumbar vertebra 42.

Spherical concave to planar adapters 100 provide a rigid interface between ball 96 of the link 12b and the slot formed upon the second end 64 of the second cross-member 14b. The spherical concave to planar adapters 100 and the ball 96 thus define a ball and socket joint which, taken along with the slot of the second cross-member 14, provide four degrees of freedom, i.e., two angular, one rotational, and one translational, between the second link 12b and the second cross-member 14b, so as to facilitate attachment of the second link 12b and second cross-member 14b to the spine at a plurality of different orientations relative to one another and relative to the spine. Washer 19 is disposed upon the threaded stud 72 intermediate nut 18 and second cross-member 14b.

The hourglass shaped bore 73 which extends through the ball 96 facilitates rotation and two angular degrees of freedom of the second link 12b relative to the threaded stud 72 anchored in the patient's spine.

Referring now to FIGS. 3 and 4, a representative link 12 comprises a first end 24 having a slot 80 formed therein and a second end 38 having an aperture 82 formed therein. An elongate mid section 84 interconnects the first end 24 and the second end 38. The slot 80 preferably comprises first 86 and second 88 recesses within which various adapters may be disposed as discussed in detail below. Providing two such recesses 86 and 88 facilitates use of the link 12 in either a bowed upwardly or bowed downwardly orientation. Each of the first 86 and 88 recesses comprise a seat 90 upon which the adapters rest. The surface finish of the seat 90, and preferably the surface finish of an adapter contacting the seat 90, both are preferably configured such that they facilitate secure maintenance of the position of the adapter relative to the link 12. More particularly, the seat 90, and preferably that surface of the adapter contacting the seat 90, are roughened, knurled, or otherwise provided with an uneven or non-smooth surface finish which tends to inhibit sliding of one surface relative to the other.

The aperture 82 is preferably configured as first 92 and second 94 truncated cones or frustums oriented with the smaller ends thereof disposed at approximately the center of the aperture 82, i.e., at the mid point of the length thereof, in a hourglass-like fashion. Such construction facilitates movement of two interconnected links 12 relative to one another while maintaining adequate structural integrity.

The second end 38 of the link 12 preferably comprises a generally spherical ball 96. By configuring the second end 38 of the link 12 in a generally spherical fashion, the ball 96 thereby may be utilized with a complimentary socket so as to provide maximum flexibility, i.e., 3 degrees of freedom, of two interconnected links 12. It is important to note that the ball 96 need not be precisely spherical in configuration, but rather may alternatively comprise a flattened tip 98 (FIG. 3), a compressed ball 97 (FIG. 5), or various other configurations typically having generally rounded surfaces.

Referring now to FIGS. 5 and 6, each link 12 is configured to facilitate attachment to another identical or similar link as well as attachment to a cross-member 14a, 14b. Generally, it would be desirable to attach the ball 96 of one link 12 to the slot 80 of another link 12 via a threaded fastener (as shown in FIGS. 1, 2, and 6).

Each spherical concave to planar adapter 100 thus fits between the slot 80 formed at the first end 24 of a link 12e and the ball 96 formed at the second end 38 of another link 12f (as shown in FIG. 6), so as to provide four degrees of freedom between the two links 12e, 12f.

As discussed above, various different finish surfaces of the contact surfaces of the adapters may be utilized to assure rigid attachment of the links 12 relative to one another. Thus, a knurled finish 102 may be utilized, preferably in combination with a similar knurled finish formed upon the seat 90 of the slot 80 which it contacts, so as to prevent slipping or undesirable change of position once the fastener 16 associated therewith is tightened. Similarly, such a finish may optionally be utilized on the concave surface 104 of the spherical concave to planar adapter 100 and preferably on the ball 96 as well. Such a roughened or knurled surface may be utilized upon any of the abutting or contacting portions of any of the various components of the spinal implant of the present invention so as to prevent relative motion thereof, as desired. Those skilled in the art will appreciate that various different surface finishes and/or configurations are similarly suitable for assuring rigid interconnection of the link 12 and cross-members 14 of the present invention.

The spherical concave to planar adapter 100 disposed within the upper cutout 86 of the link 12 shown in FIG. 5 may be used for the interconnection of another link 12 therewith, by inserting the ball 96 of another link 12 into the concave spherical surface 108 of the spherical concave to planar adapter 100, as shown in FIG. 6 and discussed in detail below.

The spherical concave to planar adapter 100 disposed within the lower cutout 88 of the link 12 shown in FIG. 5 may be utilized to attach the link to the spine or to another planar surface, such as the slot 80 of another link 12 via the use of spherical convex to planar adapter 110. Various different configurations of spherical concave to planar and spherical convex to planar adapters may be utilized to interconnect various different components of the spinal implant of the present invention, as well as components of the spinal implant of the present invention with various anatomical structures of the spine.

Referring now to FIG. 6, the interconnection of two links 12e and 12f is facilitated via the use of spherical concave to planar adapter 100 disposed within the slot 80 of link 12e which receives the ball 96 of the link 12f in a manner which facilitates longitudinal adjustment, i.e. variations in total length of the links 12e and 12f, and which also accommodates three degrees of freedom in the motion of one link 12e, 12f relative to the other link 12f, 12e. For example, the ball 96 of link 12 can easily be repositioned along the length of slot 80 of link 12e, so as to vary overall length of the assembly, the second link 12f can be rotated relative to the first link 12e, and the second link 12f can define various different angles in two perpendicular planes relative to the first link 12e.

Thus, link 12f can be rotated about its longitudinal axis, to a small degree so as to accommodate the irregular surface of the vertebra to which it is to be attached and can also be rotated about the ball 96 thereof in two different axes which are perpendicular to one another and which are perpendicular to the longitudinal axis of length 12f.

A spherical convex to planar adapter 112 is disposed within the lower cutout 88 of both links 12e and 12f, so as to facilitate attachment of the links 12e and 12f to the vertebrae. Spherical convex to planar adapters 112 provide a flat surface for the interface of the spinal implant to the spine. Optionally, the adapter utilized at the interface of the spinal implant to the spine may be configured so as to pivot in order to achieve a flush fit at the surface of the spine, such as occurs with spherical to planar adapter 112 when paired with spherical concave to spherical concave adapter 114 as mounted on the left end of link 12e.

Concave spherical to concave spherical adapter 114 facilitates the use of convex spherical to planar adapter 112 so as to provide a flat bearing surface for the nut 18 to be tightened thereagainst for link 12e. Similarly, uppermost spherical concave to planar adapter 100 provides a flat bearing surface for threaded studs 16 passing through both links 12e and 12f.

In a similar manner, spherical convex to planar adapter 116 provides a flat bearing surface for threaded stud 16 of link 12f.

Figure 7:
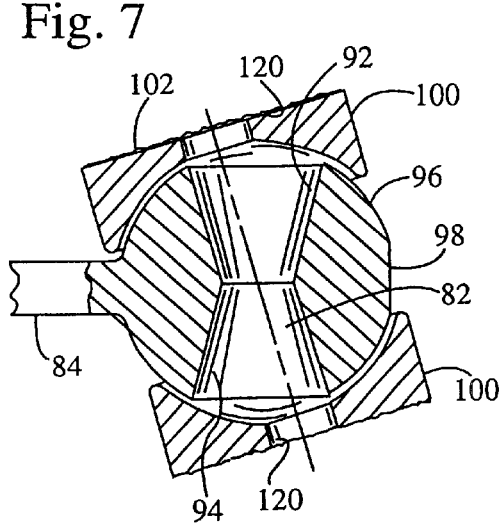
FIG. 7 is an enlarged cross-sectional side view of a ball-and-socket interface for attaching two links to one another.
Figure 8:
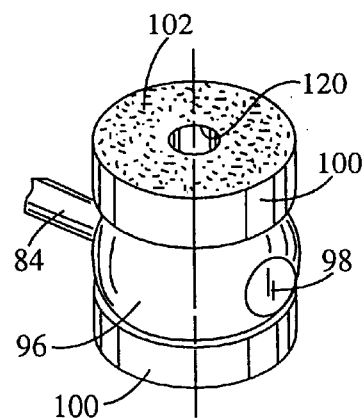
FIG. 8 is a perspective view of the ball-and-socket interface of FIG. 7.

Referring now to FIGS. 7 and 8, a ball and socket joint for interconnecting two links as illustrated. The ball and socket joint comprises a ball 96 and two spherical concave to planar adapters 100. The ball is generally spherical in configuration and optionally has a flat 98 formed thereon, as discussed above. As shown in FIG. 7, the apertures 120 of each spherical concave to planar adapter 100 are in line or on center with one another.

Figure 9:
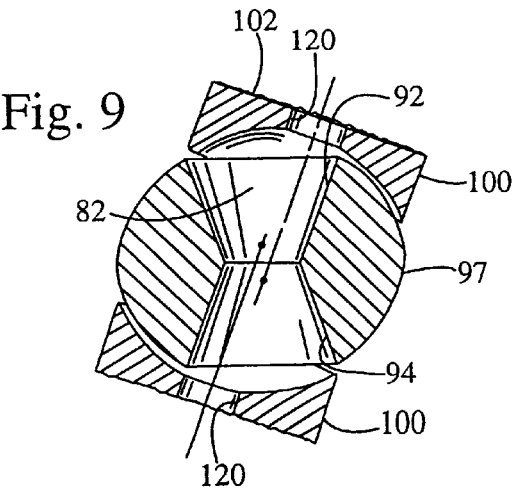
FIG. 9 is a cross-sectional side view of the ball-and-socket interface configured such that the upper and lower sockets or adapters do not have to be on center with one another and wherein the ball is somewhat compressed in the vertical direction.

Referring now to FIG. 9, a ball and socket joint comprises a compressed ball 97 and the two spherical concave to planar adapters 100 are in a non-aligned or off-center configuration.

Thus, it is clear that it is not necessary that the adapters disposed on either side of the ball 97 be oriented on center with one another or on center with the ball.

Figure 10:
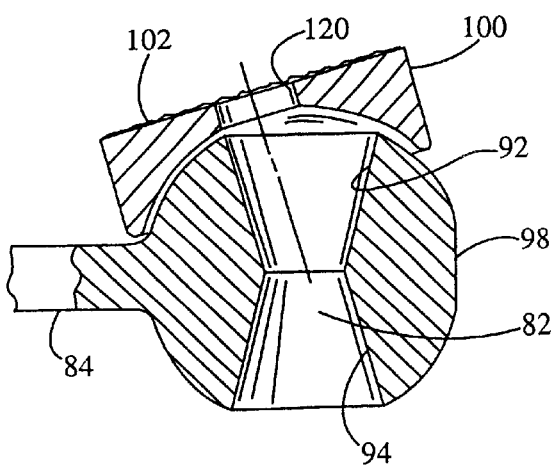
FIG. 10 is a cross-sectional side view of a ball-and-socket interface wherein the ball is somewhat elongated in the vertical direction.

Referring now to FIG. 10, optionally, only a single spherical concave to planar adapter 100 may be utilized to form the ball and socket joint, as desired.

Figure 11:
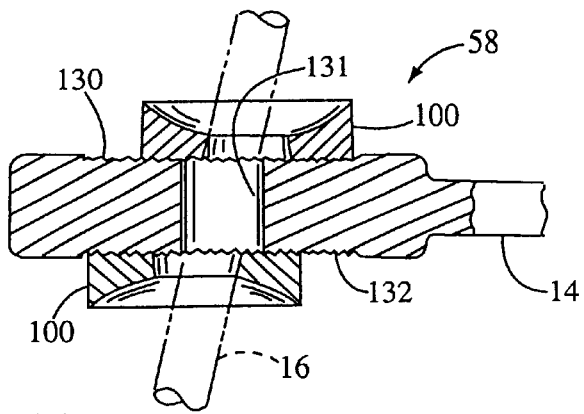
FIG. 11 is a cross-sectional side view of the slot end of a link having two planar-to-spherical adapters attached thereto.
Figure 12:
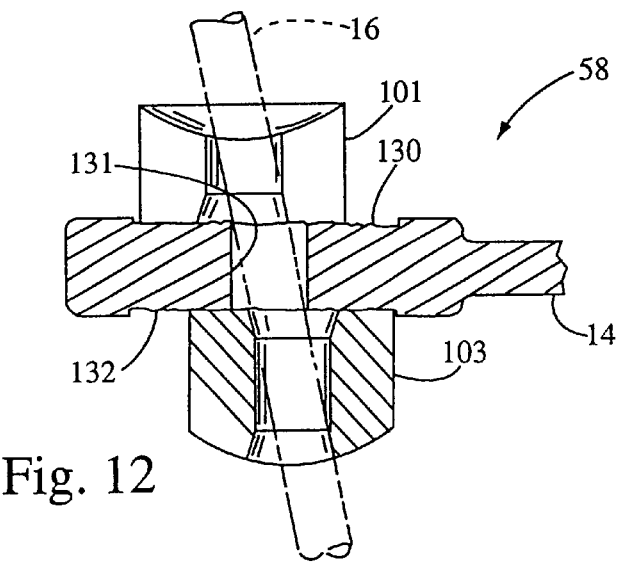
FIG. 12 is a cross-sectional side view of the slot and of a link having a planar-to-concave spherical adapter attached to the upper surface thereof and having a planar-to-convex spherical adapter attached to the lower surface thereof.
Figure 13:
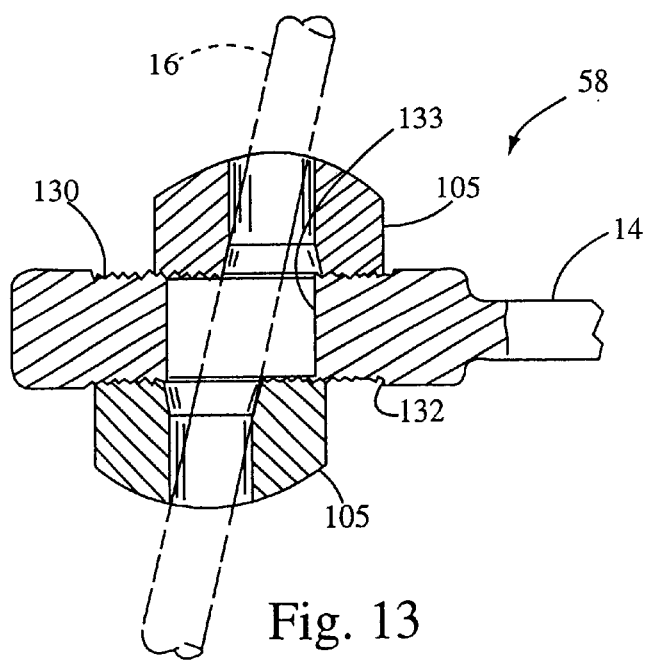
FIG. 13 is across-sectional side view of the slot end of a link having a planar-to-convex adapter attached to both the upper and lower surfaces thereof.

As shown in FIGS. 11–13, various configurations of adapters are suitable for attaching the cross-member 14 to a link 12. With particular reference to FIG. 11, the first end 58 of the cross-member 14 comprises upper 130 and lower 132 rough surfaces abutted by spherical concave adapters 100 so as to facilitate attachment to links 12, particularly via the ball 97, 98 thereof. As shown, the two spherical concave to planar adapters 100 do not need to be aligned with or on center with one another. An aperture 131 may be substituted for the slot 80, if desired.

With particular reference to FIG. 12, one spherical concave to planar adapter 101 is attached to the upper surface 130 of the link 14 and a spherical convex to planar adapter 103 is disposed upon the lower surface 132 thereof.

With particular reference to FIG. 13, a spherical convex to planar adapter 105 is disposed upon the upper surface 130 of the link 14 and substantially identical spherical convex to planar adapter 105 is disposed upon the lower surface 132 thereof. Such spherical convex to planar adapters 150 are configured to be received by the concave surface of spherical concave to planar adapters 101 as illustrated in FIG. 12. An elongate aperture or slot 133 may optionally be utilized, rather than the simple apertures 131 of FIGS. 11 and 12.

Thus, the spinal implant of the present invention can be configured in a variety of different fashions so as to accommodate the different anatomical structures of a particular patient. Those skilled in the art will appreciate that alignment of the spinal implant of the present invention is substantially simplified since it is merely necessary to place the components in position and then tighten the threaded studs so as to automatically effect proper alignment and provide the necessary rigidity. None of the components of the spinal implant of the present invention require modification, i.e., bending, in order to obtain such desired alignment.

Having described the structure of the spinal implant of the present invention in detail, it may be beneficial to describe the use thereof. The following discussion describes a procedure for the fusion of the fourth and fifth lumbar vertebrae with the sacrum as an example. This procedure is analogous to those utilized to effect fusion of various different pairs or groups of vertebrae.

First, holes are drilled in the lateral masses of the sacrum as well as the transverse processes of the fourth and fifth lumbar vertebrae at positions where the ends of the links 12 are to be located. Threaded studs 16 having self-tapping threads 70 (FIG. 2) are then threaded into the drilled holes. The threaded studs 16 optionally comprise Allen heads, socket heads or another means for applying a wrench thereto so as to facilitate such tightening. Alternatively, flat sides may be formed upon the uppermost end of the threaded studs 16 so as to facilitate such tightening. Alternatively, two nuts may be tightened together, i.e., jammed, so as to facilitate such tightening. Alternatively, a threaded socket may be utilized to effect such tightening. Those skilled in the art will appreciate that various other means for facilitating such tightening of the stud are likewise suitable.

After the threaded studs are positioned within the holes drilled into the fourth and fifth lumbar vertebrae and the sacrum, then the links 12a–d and cross-members 14a, 14b are positioned thereon along with their associated nuts, washers, and adapters, as illustrated in FIG. 1.

Those skilled in the art will appreciate that each different spinal implant may require a different configuration of adapters. However, the links and cross-members of the present invention provide standardized components suitable for use in a wide variety of different anatomical configurations. Thus, the spinal implant of the present invention may be utilized to provide rigid fixation for various different spinal fusion configurations, i.e., different vertebrae, as well as various different numbers of vertebrae. Generally, at least one spherical concave to planar adapter 100 will be utilized intermediate the slot 80 of one link and the ball 96 of another link so as to facilitate relative movement of the two links in order to accommodate the patient's particular anatomy.

Since the ball and socket interfaces and the slots 80 of the links 12 and cross-members 14 of the present invention facilitate automatic alignment thereof when the nuts 18 are tightened, the undesirable process of bending metal rods to facilitate such alignment is eliminated.

It is understood that the exemplary spinal implant described herein and shown in the drawings represents only a presently preferred embodiment of the invention. Indeed, various modifications and additions may be made to such embodiment without departing from the spirit and scope of the invention. For example, those skilled in the art will appreciate that various different configurations of the links and cross-members are suitable. The links and cross-members may have various different cross-sectional configurations, i.e., square, round, octagonal, hexagonal, triangular, etc. Although the length of each link is generally approximate that of the average distance between vertebrae, those skilled in the art will appreciate that various different lengths are likewise suitable. Further, the links and cross-members may be fabricated to provide various different amounts of bending or bowing so as to further accommodate various anatomical structures. Further, one or more of the links and one or more of the cross-members may alternatively have a slot formed upon both ends thereof or may alternatively have a ball formed upon both ends thereof.

It is further contemplated that the spinal implant of the present invention may find application in various other surgical procedures wherein it is desirable to provide rigid fixation of bones.

Further, it is contemplated that a limited amount of movement of the spine may be accommodated by eliminating use of the cross-members and utilizing links having a desired degree of flexibility. Optionally, the cross-members may be utilized during the original surgical procedure and then removed during a subsequent surgical procedure so as to facilitate movement of such flexible links. Thus, movement of the spine so as to restore a near normal degree of motion is facilitated.

Further, those skilled in the art will appreciate that the links and cross-members of the present invention may be specifically configured so as to facilitate attachment at any point along the spine.

Thus, these and other modifications and additions may be obvious to those skilled in the art and may be implemented to adapt the present invention for use in a variety of different applications.

What is claimed is:

1. A spinal implant for rigid fixation of at least two vertebrae of a spinal column, said implant comprising:
 a) a plurality of support members placeable generally longitudinally parallel to each other on opposing sides of a spinal column, with each of said support members having a generally spherical first end with a generally circular aperture therethrough having a generally hourglass-shaped side wall and a second end with an elongate slot aperture therethrough, said apertures having parallel axes whereby the circular aperture and slot aperture of longitudinally adjacent support members are alignable with each other;

b) a plurality of concave-to-planar adapters each having on one side thereof a concave surface generally complimentary in shape to the spherical first end of the support member and on the other side thereof a planar surface, with each adapter having an adapter aperture therethrough which is alignable with the circular aperture of the support member when the concave surface and spherical first end are in complimentary juxtaposition; and c) a plurality of fasteners each retainably insertable into the circular aperture, slot aperture and adapter aperture and into vertebral portions of the spinal column to thereby provide anchorage to said vertebral portions.

2. A spinal implant as claimed in claim 1 wherein at least one support member is bowed.

3. A spinal implant as claimed in claim 1 wherein the elongate slot aperture of each support member can retainably house the concave-to-planar adapter.

4. A spinal implant as claimed in claim 1 wherein each of the fasteners comprises a threaded stud.

5. A spinal implant as claimed in claim 1 wherein the support members are formed of a bio-compatible polymer composite.

6. A spinal implant as claimed in claim 5 wherein said bio-compatible polymer composite comprises carbon/polyetherether ketone composite.

7. A spinal implant for rigid fixation of at least two vertebrae of a spinal column, said implant comprising:

a) a plurality of support members placeable generally longitudinally parallel to each other on opposing sides of a spinal column, with each of said support members having a generally spherical first end with a generally circular aperture therethrough having a generally hourglass-shaped side wall and a second end with an elongate slot aperture therethrough, said apertures having parallel axes whereby the circular aperture and slot aperture of longitudinally adjacent support members are alignable with each other;

b) a plurality of concave-to-planar adapters each having on one side thereof a concave surface generally complimentary in shape to the spherical first end of the support member and on the other side thereof a planar surface, with each adapter having an adapter aperture therethrough which is alignable with the circular aperture of the support member when the concave surface and spherical first end are in complimentary juxtaposition;

c) a plurality of cross members each having a first end and a second end, with each of said first and second ends having a respective cross-member aperture therethrough wherein at least one of said cross-member apertures is elongate and wherein the cross-member aperture at the first end of a cross-member is alignable with an aperture of a support member disposed on one side of the spinal column and the cross-member aperture at the second end of said same cross-member is alignable with an aperture of a support member disposed on the other side of the spinal column; and d) a plurality of fasteners each retainably insertable into the circular aperture, slot aperture, adapter aperture and cross-member aperture and into vertebral portions of the spinal column to thereby provide anchorage to said vertebral portions.

8. A spinal implant as claimed in claim 7 wherein at least one support member is bowed.

9. A spinal implant as claimed in claim 7 wherein the elongate slot aperture of each support member can retainably house the concave-to-planar adapter.

10. A spinal implant as claimed in claim 7 wherein each of the fasteners comprises a threaded stud.

11. A spinal implant as claimed in claim 7 wherein the support members are formed of a bio-compatible polymer composite.

12. A spinal implant as claimed in claim 11 wherein the cross members are formed of a bio-compatible polymer composite.

13. A spinal implant as claimed in claim 12 wherein said bio-compatible polymer composite comprises carbon/polyetherether ketone composite.

* * * * *